United States Patent [19]

Goldman

[11] Patent Number: 5,163,419
[45] Date of Patent: Nov. 17, 1992

[54] DEVICE FOR EXPANDING THE PUPIL OF A HUMAN EYE

[76] Inventor: Kenneth N. Goldman, 301 E. 79 St., New York, N.Y. 10021

[21] Appl. No.: 680,373

[22] Filed: Apr. 4, 1991

[51] Int. Cl.$^5$ ............................................. A61B 17/02
[52] U.S. Cl. ...................................... 128/20; 128/17; 623/4; 606/107
[58] Field of Search ........................... 606/107, 198, 4; 128/17, 20; 623/4-6; 604/294, 289

[56] References Cited

U.S. PATENT DOCUMENTS

| 1,389,436 | 8/1921 | Cameron | 128/17 |
| 2,238,563 | 4/1941 | Jacques | 128/20 |
| 4,387,706 | 6/1983 | Glass | 128/20 |
| 4,428,746 | 1/1984 | Mendez | 128/20 |
| 4,782,820 | 11/1988 | Woods | 128/20 |
| 5,030,224 | 7/1991 | Wright et al. | 128/20 |
| 5,070,860 | 12/1991 | Grounauer | 128/17 |

FOREIGN PATENT DOCUMENTS

| 0655383 | 4/1979 | U.S.S.R. | 128/20 |
| 1500292 | 8/1989 | U.S.S.R. | 606/107 |

Primary Examiner—C. Fred Rosenbaum
Assistant Examiner—Ronald Stright, Jr.
Attorney, Agent, or Firm—Arthur Dresner

[57] ABSTRACT

The present invention includes a generally U-shaped body member having opposed leg portions joined by a central section. Each leg portion is connected to the central section at a pivot point for pivotal movement toward and away from each other. The body member is made of a resilient material having spring-like qualities to urge the legs away from each other. Each leg portion also has a distal end remote from the pivot points. Grooves are provided at at least three positions on the body member for engaging the inner edges of the iris of the human eye when the body member is inserted into the pupillary area. A receptor hole is located at each of the distal ends for receiving manipulative devices for causing the leg portions to be moved toward and away from each other between an expanded and a collapsed position. When the body member is in the collapsed position it may be inserted through an opening in the human eye for engagement with the iris for expansion of the pupillary area. The distance between the leg portions when in the expanded position is larger than the average diameter of the pupil of a human eye so that the pupil will expand when engaged by the leg portions.

4 Claims, 1 Drawing Sheet

DEVICE FOR EXPANDING THE PUPIL OF A HUMAN EYE

FIELD OF THE INVENTION

The present invention relates generally to the field of surgical instruments and more particularly is directed to an instrument which is used during ophthalmic surgery, such as cataract removal surgery, for use in expanding the pupillary area of the human eye to thus permit easy access by the surgeon to the lens of the eye to perform procedures required for cataract lens removal.

BACKGROUND OF THE INVENTION

During various types of ophthalmic surgical procedures temporary expansion of the pupillary area of the human eye, and maintenance of the expanded pupillary opening, is desirable in order to minimize various types of trauma or surgical incisions. One such surgical procedure typically involves an incision in the limbus area to gain access to the lens of the eye in order to remove a cataractous lens and replace the removed lens with commercially available intraocular lenses to be implanted within the posterior chamber, behind the iris.

Heretofore, such surgery typically involved the formation of a semicircular groove in and about the limbus area of the eye, which the surgeon then uses to cut through the eye forming a flap to provide access to the anterior chamber of the eye in order to remove the cataract lens. The formation of this corneal flap, which is lifted to provide access to the lens, requires a large incision involving numerous sutures and care during closure.

Alternate techniques have in recent years involved attempts to reduce incision size which has been facilitated by the use of emulsification devices in combination with foldable or reduced dimension implants. While this is an advance in the surgical procedure for cataract removal, it usually requires a dilated pupil to prevent interference with emulsification of the cataract lens. While nonsurgical techniques to dilate the pupil are typically employed, frequently mechanical expansion is required to maintain the enlarged pupil area throughout the surgical procedure.

A variety of devices have heretofore been suggested for such mechanical expansion of the pupil but many of them result in inadequate working space and frequently distort the postoperative condition of the iris.

Examples for mechanically expanding the pupil have included engaging the edges of the iris with hooks, pegs or stretching devices which invariably result in permanent deformation of the iris. Preplaced suturing followed by incisions in the iris have also been used as a means to expand the pupil. Since it is desirable to avoid unnecessary incisions this has not been met with popularity.

Another such device is illustrated in U.S. Pat. No. 4,782,820. As pointed out in this disclosure, it is desirable to expand the normal pupil area of approximately three millimeters to as large as seven to nine millimeters during operative procedures. The referenced prior art device discloses a retaining ring formed of a flexible arcuate body having a U-shaped cross section forming a side wall intended to receive the edges of the iris. A drawstring is provided to manipulate the ring so that it can contract to a size which can facilitate placement within the unexpanded pupil area and then be permitted to expand, while engaging the edges of the iris. The use of such a device however would be difficult and impracticable as it requires contraction of the ring to a size likely less than one millimeter in diameter for proper placement within the unexpanded pupil, and subsequent expansion to the required seven to nine millimeter diameter. In addition, proper placement within the unexpanded pupil appears exceedingly difficult while simultaneously trying to maintain tension on the drawstring structure.

It is accordingly a principal object of the present invention to provide a simple and easy to use device for application in ophthalmic surgery, which overcomes the disadvantages of the prior art pupillary expansion techniques while permitting cataract or other ophthalmic surgery through minimal incision procedures.

A more specific object of the present invention is to provide a pupil expander which can be easily deformed for placement within the eye through a small eye incision for engagement with the iris to accomplish pupil expansion.

Yet a further object of the present invention is to provide a human eye pupil expander made of resilient polymethylmethacrylate material to permit spring-like performance so that it can be collapsed about a hinge or pivot point for insertion through a small opening.

A still further object of the present invention is to provide a device which is capable of mechanically enlarging the pupil of a human eye without causing permanent distortion of the iris.

SUMMARY OF THE INVENTION

The foregoing objects of the present invention are generally accomplished by providing a generally U-shaped body member having opposed leg portions joined by a central section. Each leg portion is connected to the central section at a pivot point for pivotal movement toward and away from each other. Each leg section also has a distal end remote from the pivot points. Means are provided at at least there positions on the body member for engaging the iris of the human eye. Means are also carried by the distal ends for receiving manipulative devices for causing the leg portions to be moved toward and away from each other between an expanded and a collapsed position, whereby the body member, when in the collapsed position may be inserted through an opening in the human eye for engagement with the iris for expansion of the pupillary area.

The foregoing and other features of the present invention are move fully described with reference to the following drawings, annexed hereto.

DESCRIPTION OF THE INVENTION

Figures 1, 2, 3, 4:
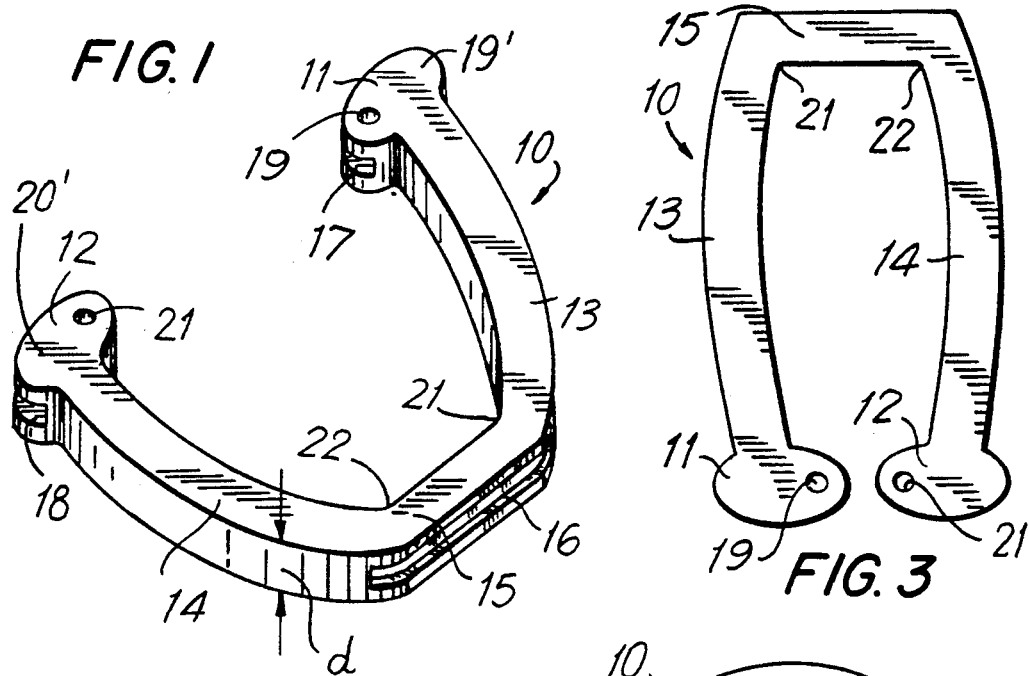
FIG. 1 is a perspective view of the present invention in its expanded condition when in use for expanding the pupil of the human eye.
FIG. 2 is a plan view of the expansion device shown in FIG. 1.
FIG. 3 is a plan view of the device shown in FIG. 1 but in a compressed condition for insertion into the eye prior to engagement with the iris.
FIG. 4 is a perspective view of the human eye showing an incision through which the device of the present invention is inserted for engagement with the iris.

Referring now in greater detail to the accompanying drawings, the device of the present invention, indicated generally by reference numeral 10 consists of a generally U-shaped body member, which in its preferred form is produced in a molding process of resilient material, such as polymethylmethacrylate. The U-shaped body member has curved leg portions 13 and 14 pivotally connected at pivot points 21 and 22 respectively to a central section 15. The leg portions carry distal ends 11 and 12.

The leg portions 13 and 14, as well as the central section 15 have a thickness "d" which is approximately one millimeter. A longitudinal groove 16 is formed in the outer wall of central section 15 which is approximately two to four millimeters long and approximately one-half millimeter thick, which is adequate for engaging the edge of the iris when the device 10 is inserted into the pupillary opening.

Each distal end 11 and 12 has an enlarged thickness to facilitate engagement by a manipulative tool, to be described hereinafter, and each end accommodates a groove 17 and 18 respectively, each groove being approximately one-half millimeter in height. The grooves 17 and 18, like the groove 16, is intended and sized for engaging an inner edge of the iris. A receptor hole 19 and 20 is located in surfaces 19' and 20' respectively of the distal ends 11 and 12 respectively for receiving pins or other engaging means of a forceps device or similar tool which can be used by the surgeon through hand manipulation to force the distal ends 11 and 12 and thereby legs 13 and 14 toward each other as a result of legs 13 and 14 pivoting about pivot points 21 and 22 respectively. When the leg portions 13 and 14 are forced together into the collapsed condition shown in FIG. 3, the device is no larger than approximately two to four millimeters across so that it can be easily inserted into an opening in the eye of less than five millimeters wide, such as illustrated in FIG. 4. When in the expanded position with legs 13 and 14 positioned as illustrated in FIG. 3, the distance between the distal ends 11 and 12 is larger than the average diameter of a human pupil and is made to be equal to the size of an expanded pupil desired by the surgeon.

With particular reference to FIG. 4 a human eye is illustrated in perspective view. An incision 25 of no more than five millimeters across can be placed to allow for insertion of the device 10 for engagement with the edges of the iris. When fully inserted through the incision 25 so that groove 16 engages the edge of the iris, the surgeon will release the tension on the forceps or other tool holding the distal ends 11 and 12 together, thus allowing the distal ends and the legs 13 and 14 to expand as a result of the spring-like nature of the material of the body member. Grooves 17 and 18 will then be placed to engage the edges of the iris at points remote from groove 16 so that the iris will now expand. Curved legs 13 and 14 may also engage the inner edge of the iris forcing it to expand creating an enlarged pupil area.

As can be appreciated from the foregoing description, the device of the present invention is simple, easy to use and can be inserted through a small incision to permit cataract or other ophthalmic surgery with the least amount of trauma and incisions.

While the present invention has been described and illustrated with respect to a certain preferred embodiment which produces satisfactory results, it will be appreciated by those skilled in the art, after understanding the purposes of the invention, that various other changes and modifications may be made without departing from the spirit and scope of the invention, and it is therefore intended to cover all such changes and modifications in the appended claims.

What is claimed is:

1. A device for expanding the pupil of a human eye comprising a generally U-shaped body member formed of a unitary construction having opposed leg portions joined by a central section, said leg portions and said central section each having a top surface, a bottom surface and a side wall therebetween, the top surfaces of each leg portion and the central section lying in the same plane, the bottom surfaces of each leg portion and said central section lying in the same plane, the planes of said top and bottom surfaces being paralleled to each other and separated by said side wall, each leg portion being connected to said central section at a pivot point for pivotal movement toward and away from each other between a collapsed position when said legs are moved toward each other and an expanded position when said legs are moved away from each other, urging means formed by said body member being made of resilient material having spring-like quality to urge said leg portions into said expanded position, each leg portion having a distal end remote from said pivot point, groove means provided at each distal end of said leg portions located in said side wall between said top and bottom surfaces and extending in a direction parallel to said top and bottom surfaces for engaging the inner edges of the iris of the human eye when said leg portions are in said expanded position, additional groove means formed in the side wall of said central section between said top and bottom surfaces thereof and extending in a direction parallel thereto for similarly engaging an inner edge of a human iris when said device is placed within the pupil area, each said groove means being substantially one-half millimeter wide in order to receive and accommodate the inner edge of a human iris, an opening in a surface of each of said distal ends of said leg portions to accommodate pin members of a tool which can be hand manipulated to effect movement of said leg portions toward each other from said expanded position into said collapsed position in opposition to said urging means, the distance between said distal ends of said leg portions when in said expanded position being between seven and nine millimeters which is greater than the three millimeter diameter of the average pupil of a human eye so that when all said groove means engage the edges of the iris said pupil will expand to at least seven millimeters, the widest distance between the leg portions being no more than four millimeters when said leg portions are in said collapsed position, whereby when said leg portions are in said collapsed position said body member may be inserted into the pupil area through an opening in the human eye of between three and five millimeters, and when said body member is so inserted and said leg portions move to said expanded position said groove means on said distal ends and said central section will engage said inner edges of the iris for expansion of the pupillary area.

2. The device according to claim 1 wherein said body member is made of polymethylmethacrylate.

3. The device according to claim 4 wherein said leg portions are curved to conform to the curve of the inner edges of the iris.

4. A device for expanding the pupil of a human eye comprising:
- a substantially U-shaped body member having opposed leg portions and an elongated central section between said leg portions;
- said leg portions and said central section each having a top surface, a bottom surface and a side wall between said surfaces, said top and bottom surfaces lying in spaced apart parallel planes;
- said leg portions being pivotally connected to opposite ends respectively of said central section, and having a distal end remote from the end connected to said central section whereby said leg portions are pivotally movable between a collapsed position when said leg portions are moved toward each other and an expanded position when said leg portions are moved away from each other, the distance between said distal ends being greater than the diameter of an average human pupil when said leg portions are in an expanded position;
- said body member being formed of a unitary construction of resilient material having spring-like qualities so that said leg portions are urged away from each other into said expanded position;
- a first groove formed in the side wall between the top and bottom surfaces of said central section extending in a direction parallel to said top and bottom surfaces, and second and third grooves formed in said distal ends located in the side wall thereof extending parallel to said top and bottom surfaces, said first, second and third grooves being sized to accept the inner edge of a human iris; and
- an opening formed in a surface of said distal end of each leg portion to accommodate manipulative means for causing said leg portions to be moved toward each other into said collapsed position in opposition to the urging of the spring-like quality of the material of the body member;
- whereby said body member may be inserted through an opening in the human eye which is less than five millimeters in width when said leg portions are in said collapsed position and whereby said first, second and third grooves will engage the inner edges of the iris when said leg portions return to the expanded position under the influence of said resilient material thereby causing expansion of the pupil area.

* * * * *